United States Patent [19]

Bournonville et al.

[11] Patent Number: 4,628,130

[45] Date of Patent: Dec. 9, 1986

[54] PROCESS FOR PRODUCING ALCOHOLS BY HYDROGENOLYSIS OF CARBOXYLIC ACID ESTERS IN THE PRESENCE OF A CATALYST CONTAINING NICKEL AND TIN, GERMANIUM OR LEAD

[75] Inventors: Jean-Paul Bournonville, Cergy Pontoise; Jean-Pierre Candy, Caluire; Gil Mabilon, St Germain en Laye, all of France

[73] Assignee: Institut Francais du Petrole, Rueil-Malmaison, France

[21] Appl. No.: 763,596

[22] Filed: Aug. 8, 1985

[30] Foreign Application Priority Data

Aug. 8, 1984 [FR] France ................................ 84 12635

[51] Int. Cl.$^4$ .................... C07C 29/136; C07C 37/055
[52] U.S. Cl. ........................ 568/885; 502/242; 502/259; 502/301; 502/326; 568/799; 568/814; 568/864
[58] Field of Search ................ 568/885, 864, 799, 814

[56] References Cited

U.S. PATENT DOCUMENTS

| 2,093,159 | 9/1937 | Schmidt | 568/885 |
| 2,322,095 | 6/1943 | Schmidt | 568/885 |
| 3,829,448 | 8/1974 | Kanetaka et al. | 568/885 |
| 4,224,248 | 9/1980 | Birdenstock et al. | 568/864 |
| 4,456,775 | 6/1984 | Travers et al. | 568/885 |

FOREIGN PATENT DOCUMENTS 95408 11/1983 European Pat. Off. ............ 568/885

OTHER PUBLICATIONS

R. Montarnal et al, "Coordination in Applied Heterogeneous Catalysts", May–Jun. 1977, vol. XXXII, No. 3, pp. 370, 371, 384.

*Primary Examiner*—J. E. Evans
*Attorney, Agent, or Firm*—Millen & White

[57] ABSTRACT

The invention has as an object the production of alcohols by hydrogenolysis of carboxylic acid esters, under hydrogen pressure, in the presence of a catalyst resulting from the incorporation of at least one compound of at least one metal from the group consisting of germanium, tin and lead to Raney nickel or to a nickel-containing carrier. The reaction is preferably conducted at a temperature from 180° to 330° C. and under a pressure from 1 to 10 MPa.

18 Claims, No Drawings

PROCESS FOR PRODUCING ALCOHOLS BY HYDROGENOLYSIS OF CARBOXYLIC ACID ESTERS IN THE PRESENCE OF A CATALYST CONTAINING NICKEL AND TIN, GERMANIUM OR LEAD

The invention concerns a catalytic process for producing alcohols by hydrogenolysis of carboxylic acid esters.

BACKGROUND OF THE INVENTION

The production of alcohols, particularly fatty alcohols, is of considerable interest in the industry.

The catalytic hydrogenolysis of carboxylic acid esters is an interesting way of producing such alcohols but, up to now, it was restrained by the disadvantages of the catalysts known in the art:

the catalysts comprising essentially mixed copper and chromium oxides, either doped or not, require operation under high pressure, nearly always higher than 20 MPa, and at a temperature ranging from 250° to 350° C.;

the catalysts comprising essentially transition metals deposited on a carrier require operation at a temperature lower than 250° C. and preferably than 200° C. in order to limit the degradation of the alcohol products to hydrocarbons; thereby requiring operating pressures generally higher than 10 MPa in order to obtain good selectivities at an acceptable conversion rate.

More recently, in the European patent application No. EP-A-95 408 a catalyst has been proposed which is formed by the association of rhodium with, for example, tin, deposited on such a carrier as, for example, silica or alumina. By using this catalyst, the operating conditions may be relatively mild (temperature lower than about 280° C. and pressure lower than about 8 MPa) with good yields of alcohols. However, the high cost and the limited availability of rhodium are serious disadvantages and, accordingly, the applicant has continued searching in order to find a catalyst giving good yields of alcohols under relatively mild operating conditions without the disadvantages of rhodium use.

SUMMARY OF THE INVENTION

It has been discovered, surprisingly, that it was possible to an hydrogenate an ester to alcohol in the presence of a catalyst containing nickel and at least one second element selected from the group consisting of tin, germanium and lead, said catalyst resulting from the incorporation of at least one compound of at least one metal from the Sn, Ge and Pb group to a nickel-containing carrier or to Raney nickel but with the exclusion of nickel-aluminum alloy used to form Raney nickel. The esters of carboxylic acids which may be converted to alcohols are advantageously selected from the group of esters of monocarboxylic acids, for example esters of acetic, propionic, butyric, valeric, caproic, oleic, or palmitic acids, or of polycarboxylic acids, particularly dicarboxylic acids such as for example, the esters of oxalic, malonic or adipic acids, said acids being esterified with linear or branched alkyl alcohols such for example as methanol or ethanol or aralkyl alcohols such for example as benzyl alcohol or hydroxy aromatic compounds such for example as phenol. It is also possible to hydrogenate cyclic esters, particularly lactones, for example valerolactone or caprolactone. The hydrogenation of an ester of carboxylic monoacid with a monoalcohol, without modifying the structure of the hydrocarbon chain, is represented by the following equation:

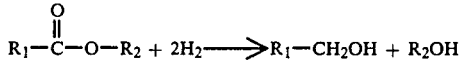

wherein $R_1$ is a saturated or unsaturated hydrocarbyl radical having 1 to 30 carbon atoms, for example a $C_1$-$C_{20}$ alkyl radical, a $C_6$-$C_{22}$ aryl radical or a $C_7$-$C_{30}$ aralkyl radical and wherein $R_2$ is a $C_1$-$C_{30}$ hydrocarbyl radical, e.g. a $C_6$-$C_{22}$ aryl radical, a $C_7$-$C_{30}$ aralkyl radical or a $C_1$-$C_{20}$ alkyl radical, $R_2$ being preferably a $C_1$-$C_{10}$ alkyl radical and more preferably a methyl or ethyl radical.

The operation is conducted continuously or batchwise in a reactor, preferably under a total pressure from 10 to 100 bars (1 to 10 megapascals) and more preferably under a total pressure from 30 to 80 bars (3 to 8 MPa), although higher pressures, for example up to 300 bars, can be used without disadvantage. The temperature is advantageously from 180° to 330° C. and preferably from 200° to 280° C. and the molar ratio of hydrogen to ester ranges for example from 2:1 to 50:1 and more advantageously from 2:1 to 5:1. The reaction is performed in the presence of a supported metal catalyst containing the following elements: nickel in a proportion by weight selected from 0.1 to 60% and preferably from 2 to 10% and at least one element selected from the group consisting of germanium, tin and lead, in a proportion by weight from 0.1 to 20% and more particularly from 1.5 to 12%. Two of the metals from the above mentioned group or even three metals of this group may be advantageously used together. The carrier, if any, may be selected from the group consisting of silica, different types of alumina, silica aluminas, aluminates of elements from groups $I_A$, $II_A$ or $II_B$ of the periodic classification of elements, such for example as Ca, Mg, Ba, Zn, Na, K, Cd aluminates and mixed aluminates and coal, and preferably from the group consisting of silica and aluminates of alkali and/or alkaline-earth metals and/or zinc and/or cadmium and mixed aluminates.

It is particularly advantageous to use catalysts wherein the atomic ratio of the one or more elements from the Sn, Ge and Pb group to nickel in the catalyst is from 0.01:1 to 4:1 and preferably from 0.1:1 to 1:1.

The catalyst may be prepared by different methods for impregnating the carrier and the invention is not limited to a particular method. The impregnation may be performed, for example, by contacting the performed carrier with an aqueous or organic solution of a compound of the one or more selected metals, the volume of solution being preferably in excess with respect to the retention volume of the carrier or equal to said volume. Nickel and the additional metal may be introduced simultaneously or successively. After having maintained the carrier in contact with the solution for several hours, the impregnated carrier is filtered, washed with distilled water, dried and roasted in air between 110° and 600° C., preferably between 110° and 500° C. Before use, the catalyst is reduced with hydrogen at a temperature from 200° to 600° C. and preferably from 300° to 500° C., this reduction being performed either immediately after roasting or subsequently by the user.

The element selected from the group consisting of tin, germanium and lead may be introduced as aqueous solution or as hydrocarbon solution, according to the nature of the precursor.

Preferably, the catalyst is obtained by impregnating the carrier with an aqueous or organic solution of at least one nickel compound, the volume of the solution being preferably in excess with respect to the retention volume of the carrier or equal to said volume. The impregnated carrier is then filtered, optionally washed with distilled water, then dried and roasted in air at a temperature from about 110° C. to about 600° C., preferably from about 110° C. to about 500° C., then reduced with hydrogen at a temperature from about 200° C. to about 600° C., preferably from about 300° C. to about 500° C., the resultant product being then impregnated with an aqueous or organic solution of a germanium, tin and/or lead compound. More advantageously a solution of at least one hydrocarbyl-germanium, hydrocarbyl-tin or hydrocarbyl-lead compound in a saturated hydrocarbon is used. After having maintained contact between the carrier impregnated with nicked and the solution containing at least one compound of germanium, tin or lead, for several hours, the product is filtered, optionally washed with the solvent used for depositing germanium, tin and/or lead, dried and optionally roasted in air at a temperature from about 110° C. to about 600° C., preferably from about 110° C. to about 500° C. Before use, the catalyst is reduced with hydrogen at a temperature from about 200° C. to about 600° C., preferably from about 300° C. to about 500° C., this reduction being performed either immediately after roasting or subsequently by the user.

Another method consists of mixing wet carrier powder with catalyst precursors and then shaping and drying.

Examples of metal precursors useful for manufacturing the catalyst are as follows:

For nickel, such compounds as chloride, nitrate or salts of organic acids soluble in the impregnation solvent, e.g. nickel chloride, nickel nitrate, organic acid salts such as nickel acetate, but also nickel hexamine chloride or nitrate, can be used. Also nickel organometallic compounds dissolved in a hydrocarbon, for example in a saturated paraffinic hydrocarbon containing 5–12 carbon atoms, in a naphthenic hydrocarbon containing 6–12 carbon atoms or in an aromatic hydrocarbon containing 6–11 carbon atoms, can be used, for example the dimethylglyoxime derivative, nickel stearate, nickel dicyclopentadienyl or nickel dicyclopentadiene and preferably nickel acetylacetonate.

The element selected from the group consisting of tin, germanium and lead may be introduced by means of intermediate compounds such as tin chlorides, bromides and nitrate, lead halides, nitrate and acetate, germanium chloride and oxalate in aqueous or organic solution or preferably as hydrocarbyl metals such as alkyl or aryl metals of tin, germanium and lead, for example: tetraethyl-tin, tetramethyl-tin, tetrapropyl-germanium, tetraethyl-lead, diphenyl-tin, diphenyl-germanium, tetraphenyl-lead, advantageously as hydrocarbon solution.

The carrier may be of various type, as already mentioned above. A particularly well-adapted carrier has specific characteristics such as a specific surface, determined by the B.E.T. method, ranging from 10 to 500 square meters per gram and preferably from 50 to 500 square meters per gram and a total pore volume from 0.2 to 1.3 cm$^3$/g of carrier and preferably from 0.5 to 1.1 cm$^3$/g of carrier.

Once the metals are fixed on the carrier, the catalyst is advantageously subjected to an activation treatment with hydrogen at high temperature, for example 300°–500° C., so as to obtain an active metal phase. The treatment with hydrogen consists for example of slowly increasing the temperature under a hydrogen stream, up to the maximum reduction temperature, ranging, for example from 300° to 500° C. and preferably from 350° to 450° C., this temperature being then maintained for 1 to 6 hours.

An active metal catalyst is also obtained from a product of the Raney nickel type, i.e. consisting at least partly of Raney nickel, such for example, as a product containing a conventional dehydrogenating metal, generally pertaining to group VIII of the periodic classification of elements, for example cobalt associated with Raney nickel, to which is added at least one compound of a metal or at least one metal from the group formed of germanium, tin and lead.

The presence of at least one additional metal from the Ge, Sn, Pb group results in a substantial decrease of parasitic reactions, particularly in a decrease of hydrocarbon formation.

The introduction of at least one additional metal is advantageously performed by injecting the one or more additional metals in the reaction zone at the reaction temperature, the catalyst precursor which contains Raney nickel being suspended into the reaction liquid phase. The introduction of the additional metal into the reaction medium is advantageously performed by means of a solution of at least one organometallic compound of at least one of the metals from the tin, lead and germanium group. The one or more organometallic compounds used for preparing the catalyst is (are) preferably selected from the group consisting of tin, germanium and/or lead alkylmetals, arylmetals, alkylarylmetals and aralkylmetals. The amount of metal to add is generally from 0.1 to 20% by weight (expressed as elemental metal) and advantageously from 0.5 to 10% of the weight of Raney nickel.

EXAMPLES

The following non limitative examples illustrate the invention.

EXAMPLE 1

The catalyst is prepared in two steps:

fixation of nickel, by impregnation with an ammonia solution of nickel acetate, on silica of specific surface equal to 280 m$^2$ per gram and of total pore volume equal to 80 cc per 100 grams, followed with a filtration, a drying at 110° C., a roasting in air at 450° C. and a reduction in hydrogen at 450° C.

fixation of tin on the roasted and reduced carrier preimpregnated with nickel, by means of tetraethyl-tin dissolved in normal heptane. After having maintained the catalyst in contact for 4 hours with the tetraethyl-tin solution at heptane reflux, the catalyst is washed with heptane and dried.

The catalyst is then fed to a tubular reactor and reduced for 4 hours at 300° C. in hydrogen stream.

The operating conditions for ethyl acetate hydrogenolysis are as follows:

pressure: 50 bars (5.0 MPa)
Wt/Wt/h: 4 kg/kg of catalyst/h molar ratio H₂/ester:5

In said first series of tests the tin content of the catalysts was varied, starting from an initial catalyst containing 2.5% by weight of nickel. The working temperature was 250° C.

The results are given in table 1.

TABLE I

| Ni (% b.w.) | Sn (% b.w.) | Total conversion (% by weight) | yield (ethanol) (% by weight) |
|---|---|---|---|
| 2.5 | 0 | 42 | 0.9 |
| 2.5 | 0.5 | 3.5 | 2.4 |
| 2.5 | 0.8 | 6.2 | 5.8 |
| 2.5 | 1.5 | 14 | 13.1 |
| 2.5 | 2.3 | 26.2 | 22.9 |
| 2.5 | 2.6 | 32.1 | 31.1 |
| 2.5 | 3.0 | 37.5 | 36.4 |
| 2.5 | 10.0 | 22.0 | 21.9 |

EXAMPLE 2

The catalytic properties, for hydrogenolysis of ethyl acetate, of two catalysts have been compared at different temperatures: one of these catalysts contains 2.5% of nickel on the silica of example 1 and the other 2.5% of nickel and 3.0% of tin on the same silica carrier. All other conditions are identical to those of example 1. The results are given in table 2.

TABLE 2

| | Catalyst | | | |
|---|---|---|---|---|
| | 2.5% Ni/SiO₂ | | 2.5% Ni + 3% Sn/SiO₂ | |
| Temperature (°C.) | Conversion (% b.w.) | Yield (ethanol) (% b.w.) | Conversion (% b.w.) | Yield (ethanol) (% b.w.) |
| 200 | 2.3 | 1.6 | 14.2 | 14.1 |
| 220 | 19 | 5.8 | 23.8 | 23.7 |
| 250 | 42 | 0.9 | 37.5 | 36.4 |
| 280 | 99.8 | 0 | 49.5 | 46.5 |

Within the temperature range considered the bimetallic catalyst of nickel-tin deposited on silica is incomparably more selective for producing alcohol.

EXAMPLE 3

The purpose is to manufacture ethanol from ethyl acetate at different temperatures by means of two different catalysts: one of these catalysts (A) contains 2.5% of nickel and 3.0% of tin on silica prepared according to the method described in example 1, the other (B), containing 2.5% of nickel and 3.0% of tin, is prepared in two steps as follows:

1st step

Fixation of nickel by impregnating with an ammonia solution of nickel acetate a silica of 280 m²×g⁻¹ specific surface and of 0.8 cc×g⁻¹ total pore volume, followed with filtration, drying at 110° C., roasting in air at 450° C. and reduction with hydrogen at 450° C.

2nd step

Fixation of tin on the roasted and reduced carrier, preimpregnated with nickel, by means of an aqueous solution of stannous chloride, while maintaining the pH at a value of 0.5 pH unit by adding hydrochloric acid. The volume of the solution is equal to the pore volume of silica. After 4 hours of contact between the tin precursor solution and the catalyst precursor obtained in step 1, at room temperature, the catalyst is dried.

The two catalysts A and B are then activated in a hydrogen stream at 300° C. for 4 hours, then tested in the following conditions:
Pressure: 50 bars (5.0 MPa)
Wt/Wt/h: 4 kg/kg of catalyst/h
Molar ratio H₂/ester:5
Variable temperature.

The results are given in table 3

TABLE 3

| | CATALYST | | | |
|---|---|---|---|---|
| | A | | B | |
| Temperature °C. | Conversion % b.w. | Yield ethanol % bw | Conversion % b.w. | Yield ethanol % bw |
| 200 | 14.2 | 14.1 | 16.5 | 12.7 |
| 220 | 23.8 | 23.7 | 28.2 | 20.7 |
| 250 | 37.5 | 36.4 | 48.4 | 31.3 |
| 280 | 49.5 | 46.5 | 61 | 39.5 |

Within the whole considered temperature range the catalyst prepared from tetraethyl-tin appears as more selctive than that prepared from stannous chloride.

EXAMPLE 4

The purpose is to manufacture ethanol from ethyl acetate under conditions identical to those of example 1. The catalyst comprises nickel (2.5%) deposited on the silica of example 1 and a second element from the tin, germanium and lead group.

Germanium and lead are impregnated in hydrocarbon solution (normal-heptane) respectively as tetraethyl-germanium and tetraethyl-lead. The tin catalyst has been described in example 1.

The so-prepared catalysts are used in the same conditions as in example 1 (T: 250° C., P: 50 bars, Wt/Wt/h: 4, molar ratio H₂/ester:5).

The results are given in table 4.

TABLE 4

| Ni (% b.w.) | 2nd metal (% b.w.) | Conversion (% b.w.) | Yield (ethanol) (% b.w.) |
|---|---|---|---|
| 2.5 | 0 | 42 | 0.9 |
| 2.5 | Sn = 3.0 | 37.5 | 36.4 |
| 2.5 | Ge = 1.8 | 36.9 | 35.7 |
| 2.5 | Pb = 5.2 | 37.1 | 36.0 |

Tin may be thus replaced with germanium and lead without significant change in the catalytic properties of the active mass.

EXAMPLE 5

Catalysts of nickel and tin on carriers containing aluminates of alkali or alkaline-earth metals, zinc or cadmium are prepared according to the method described in example 1. These carriers are specific surfaces from 80 to 150 square meters per gram and pore volumes ranging from 50 to 100 cc per 100 grams. The respective percentages of nickel and tin are given in table 5.

The hydrogenolysis of ethyl acetate has been performed in the same conditions as in example 1. The results are summarized in table 5.

TABLE 5

| Carrier | Ni (% bw) | Sn (% bw) | Conversion (% bw) | Yield to ethanol (% bw) |
|---|---|---|---|---|
| Sodium aluminate | 2.5 | 3.1 | 35.8 | 34.7 |
| Potassium aluminate | 2.5 | 3.2 | 36.1 | 35 |

TABLE 5-continued

| Carrier | Ni (% bw) | Sn (% bw) | Conversion (% bw) | Yield to ethanol (% bw) |
|---|---|---|---|---|
| Magnesium aluminate | 2.5 | 3.0 | 35.6 | 34.9 |
| Calcium aluminate | 2.5 | 2.9 | 35.9 | 35.2 |
| barium aluminate | 2.5 | 3.1 | 36.0 | 35.6 |
| zinc aluminate | 2.5 | 3.0 | 35.7 | 35.3 |
| cadmium aluminate | 2.5 | 3.0 | 36.2 | 35.1 |
| Mg and Ca aluminates | 2.5 | 3.0 | 35.7 | 35.2 |
| Ca and Ba aluminates | 2.5 | 2.9 | 36.1 | 35.7 |
| Zn and Mg aluminates | 2.5 | 3.2 | 36.0 | 35.5 |

Accordingly, aluminates of alkali or alkaline-earth metals and/or zinc and/or cadmium can be advantageously used as catalyst carriers.

EXAMPLE 6

The purpose is to manufacture different alcohols from various esters in the presence of a catalyst containing nickel (2.5%) and tin (3%) deposited on silica and in operating conditions identical to those of example 1.

The following esters have been used:
secondary butyl acetate
amyl acetate
hexyl acetate
ethyl caprate
methyl palmitate
methyl oleate.

The results are summarized in table 6.

TABLE 6

| Substrate | Obtained alcohols | Conversion (% b.w.) | Alcohols yield (% b.w.) |
|---|---|---|---|
| Secondary butyl acetate | Ethanol and 2-butanol | 36.3 | 35.1 |
| Amyl acetate | Ethanol and amyl alcohol | 34.5 | 33.1 |
| Hexyl acetate | Ethanol and 1-hexanol | 36.1 | 34.8 |
| Ethyl caprate | 1-Decanol and ethanol | 35.5 | 33.9 |
| Methyl palmitate | 1-Hexadecanol & methanol | 33.1 | 31.7 |
| Methyl oleate | 1-Octadecanol & methanol | 34.2 | 33.0 |

EXAMPLE 7

A suspension of Raney nickel (10 grams) in 100 ml ethyl acetate, at ordinary temperature, is introduced into a reactor of Grignard type of 500 ml capacity, withstanding high pressures (up to 80 bars), provided with a stirring system and temperature and pressure control and regulation systems, while injecting, under stirring, a solution of tetrabutyl-tin in ethyl acetate in such amount that the tin content of the liquid reaction phase is equal to 10% by weight of the total Raney nickel weight. The suspension is progressively heated, under constant stirring, up to 220° C.; when said temperature is attained, hydrogen is introduced under pressure so as to obtain a total pressure of 50 bars. After one hour of reaction at 220° C. under a pressure of 50 bars, the reaction product is recovered. The composition of the reaction effluent, after expansion to atmospheric pressure of the reactor content, is determined by analysis of the gaseous and liquid phases. The main constituents are:

methane: 0.2% by weight
ethane: 0.6% by weight
ethanol: 79% by weight
ethyl acetate: 20.2% by weight The selectivity to ethanol is 99%.

EXAMPLE 8 (comparative)

Ethyl acetate is reduced in the same reactor as that used in example 6 and in the same operating conditions except that no tin is introduced. The composition of the reaction effluent, after expansion of the reactor content to atmospheric pressure, is determined by analysis of the gaseous and liquid phases. The main constituents are as follows:

methane: 25.3% by weight
ethane: 8.5% by weight
ethanol: 18% by weight
ethyl acetate: 48.2% by weight The selectivity to ethanol is 34.7%.

What is claimed as the invention is:

1. A process for manufacturing alcohols, wherein a carboxylic acid ester is treated with hydrogen in the presence of a catalyst containing nickel and at least one second element selected from the group consisting of germanium, tin and lead, characterized in that the catalyst results from the incorporation of at least one hydrocarbyl compound of at least one germanium, tin and lead metal to Raney nickel or a nickel-containing carrier.

2. A process according to claim 1, wherein the catalyst comprises a carrier and from 0.1 to 60% by weight of nickel and 0.1 to 20% by weight of at least one of germanium, tin or lead.

3. A process according to claim 1, wherein the atomic ratio of Sn, Ge or Pb to nickel is from 0.01:1 to 4:1.

4. A process according to claim 1, wherein the catalyst contains Raney nickel and, in proportion to Raney nickel, from 0.1 to 20% by weight of at least one of germanium, tin and lead group.

5. A process according to claim 1, wherein the carrier has a surface from 10 to 500 m$^2$/g and a pore volume from 0.2 to 1.3 cc/g.

6. A process according to claim 1, wherein the nickel-containing carrier is silica.

7. A process according to claim 1, wherein the nickel-containing carrier is alumina, an aluminate or a mixed aluminate of an element from groups $I_A$, $II_A$ or $II_B$ of the periodic classification of elements.

8. A process according to claim 1, wherein the catalyst is obtained by impregnation of a carrier with an aqueous or organic solution of at least one nickel compound, drying of the impregnated carrier followed with roasting at a temperature from about 110° C. to about 600° C., then with reduction in hydrogen at a temperature from about 200° C. to about 600° C. and finally with the introduction of at least one hydrocarbyl compound of at least one metal of the group consisting of germanium, tin and lead.

9. A process for manufacturing alcohols according to claim 1, wherein the pressure ranges from 1 to 30 MPa, the temperature from 180° to 330° C. and the molar ratio hydrogen/ester from 2:1 to 50:1.

10. A process according to claim 1, wherein the carboxylic acid ester has the formula

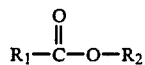

wherein $R_1$ and $R_2$ are each independently $C_{1\text{-}20}$-alkyl, $C_{6\text{-}22}$-aryl or $C_{7\text{-}30}$ aralkyl.

11. A process according to claim 10, wherein the carboxylic acid ester is an ester of acetic, propionic, butyric, valeric, caproic, oleic, palmitic, oxalic, malonic or adipic acid.

12. A process according to claim 11, wherein the carboxylic acid ester is produced by esterifying said acid with methanol, ethanol, benzyl alcohol or phenol.

13. A process according to claim 1, wherein the carboxylic acid ester is valerolactone or caprolactone.

14. A process according to claim 1, wherein the hydrocarbyl compound of germanium, tin or lead is incorporated into the Raney nickel or nickel-containing carrier as a hydrocarbon solution thereof.

15. A process according to claim 14, wherein the hydrocarbon solution is a solution of a saturated hydrocarbon.

16. A process according to claim 15, wherein the hydrocarbyl compound is tetraethyl tin and the hydrocarbon solution is n-heptane.

17. A process according to claim 15, wherein the hydrocarbyl compound is a mixture of tetraethyl germanium and tetraethyl lead and the hydrocarbon solution is n-heptane.

18. A process according to claim 14, wherein the hydrocarbyl compound is tetrabutyl tin and the hydrocarbon solution is ethyl acetate.

* * * * *